(12) United States Patent
Rogers et al.

(10) Patent No.: US 7,468,506 B2
(45) Date of Patent: Dec. 23, 2008

(54) SPOT GRID ARRAY SCANNING SYSTEM

(75) Inventors: Steven R. Rogers, Emek Sorek (IL); Nissim Elmaliach, Raanana (IL); Emanuel Elyasef, Rehovot (IL); Alon Litman, Nes Lidna (IL); Ron Naftali, Shoham (IL)

(73) Assignee: Applied Materials, Israel, Ltd., Rshovot (IL)

( * ) Notice: Subject to any disclaimer, the term of this patent is extended or adjusted under 35 U.S.C. 154(b) by 2 days.

(21) Appl. No.: 11/334,963

(22) Filed: Jan. 19, 2006

(65) Prior Publication Data

US 2006/0261261 A1 Nov. 23, 2006

Related U.S. Application Data

(60) Provisional application No. 60/647,970, filed on Jan. 26, 2005.

(51) Int. Cl.
*H01J 3/14* (2006.01)
*H01J 5/16* (2006.01)
*H01J 40/14* (2006.01)

(52) U.S. Cl. .................. 250/234; 250/235; 250/559.16; 250/559.22; 356/601

(58) Field of Classification Search .................. 250/234, 250/235, 559.16, 559.22; 356/601
See application file for complete search history.

(56) References Cited

U.S. PATENT DOCUMENTS 5,892,224 A 4/1999 Nakasuji

| | | | | |
|---|---|---|---|---|
| 5,973,332 A * | 10/1999 | Muraki et al. | ............ | 250/492.2 |
| 6,028,306 A * | 2/2000 | Hayashi | ....................... | 250/235 |
| 6,465,783 B1 * | 10/2002 | Nakasuji | ..................... | 250/311 |
| 6,504,147 B1 * | 1/2003 | Ito et al. | ..................... | 250/234 |
| 6,593,152 B2 | 7/2003 | Nakasuji et al. | | |
| 6,740,896 B2 * | 5/2004 | Nagamura | ............. | 250/559.45 |
| 6,936,810 B2 | 8/2005 | Benedict | | |
| 7,067,830 B2 * | 6/2006 | Yoda et al. | ............. | 250/492.22 |
| 7,095,022 B2 | 8/2006 | Nakasuji et al. | | |
| 7,109,483 B2 | 9/2006 | Nakasuji et al. | | |
| 7,129,485 B2 | 10/2006 | Nakasuji et al. | | |
| 7,135,676 B2 | 11/2006 | Nakasuji et al. | | |
| 7,223,973 B2 | 5/2007 | Kimba et al. | | |
| 7,244,932 B2 | 7/2007 | Nakasuji et al. | | |
| 7,244,949 B2 | 7/2007 | Knippelmeyer et al. | | |
| 7,247,848 B2 | 7/2007 | Nakasuji et al. | | |
| 2001/0052576 A1 | 12/2001 | Shimada et al. | | |
| 2001/0054690 A1 | 12/2001 | Shimada et al. | | |

(Continued)

FOREIGN PATENT DOCUMENTS

WO 2005/024881 A2 3/2005

(Continued)

*Primary Examiner*—Seung C. Sohn
(74) *Attorney, Agent, or Firm*—Tarek N. Fahmi

(57) ABSTRACT

A method for scanning a surface, consisting of focusing an array of beams using optics having an axis, so as to irradiate a region of the surface intercepted by the axis, such that each beam irradiates a portion of a respective sub-region within the region. The method further includes moving at least one of the array and the surface so as to cause a translation of the surface relative to the axis in a first direction. During the translation in the first direction, each of the beams is scanned over the respective sub-region in a second direction, which is different from the first direction.

20 Claims, 10 Drawing Sheets

U.S. PATENT DOCUMENTS

| | | |
|---|---|---|
| 2002/0028399 A1 | 3/2002 | Nakasuji et al. |
| 2002/0033449 A1 | 3/2002 | Nakasuji et al. |
| 2002/0109090 A1 | 8/2002 | Nakasuji et al. |
| 2002/0130262 A1 | 9/2002 | Nakasuji et al. |
| 2002/0142486 A1 | 10/2002 | Yanagawa et al. |
| 2002/0148961 A1 | 10/2002 | Nakasuji et al. |
| 2003/0156280 A1 | 8/2003 | Reinhorn |
| 2003/0179369 A1 | 9/2003 | Feldman et al. |
| 2003/0184835 A1 | 10/2003 | Goldberg et al. |
| 2003/0227618 A1 | 12/2003 | Some |
| 2004/0119023 A1 * | 6/2004 | Nakasuji et al. ......... 250/396 R |
| 2005/0024881 A1 | 2/2005 | Lin |
| 2005/0074002 A1 | 4/2005 | Yoakum et al. |
| 2006/0012791 A1 | 1/2006 | Reinhorn et al. |
| 2006/0023205 A1 | 2/2006 | Elyasef et al. |
| 2006/0060789 A1 | 3/2006 | Rogers |
| 2006/0261261 A1 | 11/2006 | Rogers et al. |
| 2006/0289804 A1 | 12/2006 | Knippelmeyer et al. |
| 2007/0028595 A1 | 2/2007 | Mongia et al. |
| 2007/0028596 A1 | 2/2007 | Takaku et al. |
| 2007/0060017 A1 | 3/2007 | Klusmeyer et al. |
| 2007/0133077 A1 | 6/2007 | Rogers et al. |

FOREIGN PATENT DOCUMENTS

| | | |
|---|---|---|
| WO | 2005/103657 | 11/2005 |

* cited by examiner

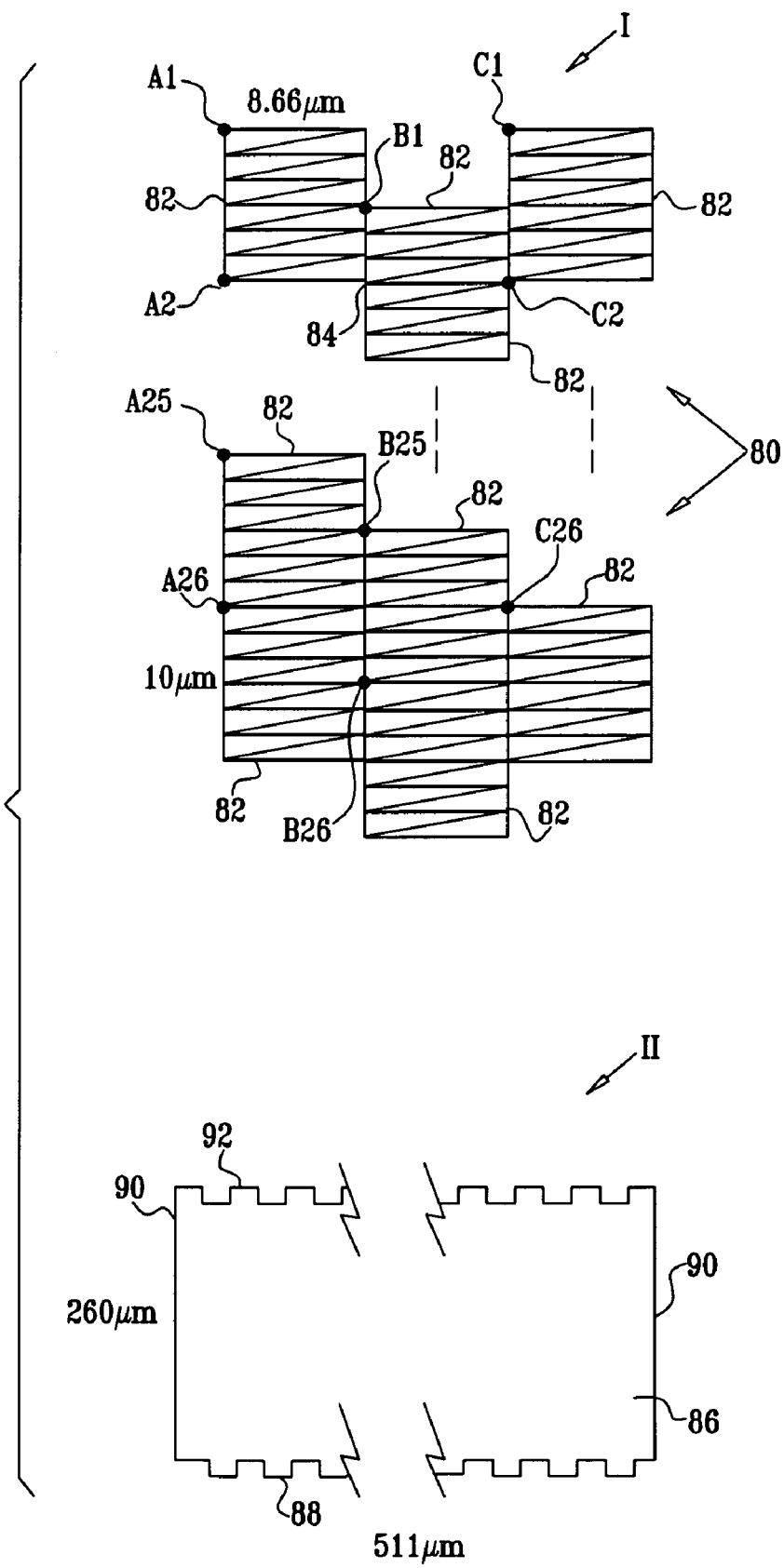

SPOT GRID ARRAY SCANNING SYSTEM

CROSS-REFERENCE TO RELATED APPLICATION

This application claims the benefit of U.S. Provisional Patent Application 60/647,970, filed Jan. 26, 2005, which is incorporated herein by reference.

FIELD OF THE INVENTION

The present invention relates generally to semiconductor wafer fabrication, and specifically to inspection and/or production of the wafer, and/or of elements used for the wafer fabrication.

BACKGROUND OF THE INVENTION

In the fabrication of a semiconductor wafer, as well as in the production of elements, such as reticles, used in the fabrication, there are typically a large number of steps. Each of these steps is time-consuming, and for efficient fabrication it is important to minimize the time taken while maintaining the quality of the steps. For example, in inspecting the wafer during or at conclusion of the fabrication, a number of methods for minimizing the inspection time are known in the art.

Inspection may be performed by scanning the wafer with a particle or an electromagnetic wave beam, and observing properties of the beam after it has interacted with the wafer, typically with the wafer surface. Typically the beam is used to generate an image of the wafer surface. The scanning and/or imaging inspection time may be reduced by using multiple inspection beams, each beam having generally similar properties. The beams are focused onto the wafer surface, and are scanned across the surface in tandem. Using a multiplicity of inspection beams produces a corresponding saving in time to scan and/or image the wafer surface, compared to the time taken if only a single beam is used.

PCT Application WO 03/040709, to Almogy, et al., whose disclosure is incorporated herein by reference, describes an optical imaging system which uses a plurality of optical beams from a spot grid array, the beams being focused onto the surface of a wafer. The wafer is moved so that the focused spots continuously and linearly traverse the surface. The spots are offset relative to each other so that the traversed lines followed by adjacent spots do not overlap, but do touch each other. One scan of the array thus images a relatively large swathe of the wafer.

PCT Application WO 03/041109, to Almogy, et al., whose disclosure is incorporated herein by reference, describes an electron beam imaging system which uses a plurality of electron beams from a spot grid array. The operation of the electron beam imaging system is generally similar to that of the optical imaging system of PCT Application WO 03/040709.

PCT Application WO 2005/024881, to Knippelmeyer, et al., whose disclosure is incorporated herein by reference, describes a charged particle beam imaging system which uses a plurality of charged particle beams from a spot grid array arranged in a pattern. The system includes an element which acts on the charged particle beams so as to affect the regularity of the pattern from the array. The element may be adjusted to increase the regularity of the pattern, in cases where the pattern regularity has decreased by passage of the beams through the system.

SUMMARY OF THE INVENTION

In embodiments of the present invention, an array of beams is focused to an array of respective spots on a surface, typically for the purpose of inspection and/or lithography of the surface. The surface is moved linearly in its own plane, and the array of spots is moved in the plane in a discontinuous manner so that the spots remain within an optimal focusing region of the plane. The motions of the array and of the surface are set so that the array of spots irradiate a swathe of the surface, parallel to the linear motion of the surface, while continuing to be focused onto the surface within the optimal focusing region. The motions are also set so that substantially every point within the swathe is irradiated by at least one of the spots. All of the swathe may thus be irradiated in an efficient manner.

In one embodiment, the surface moves with a constant velocity, and the array of spots is moved with a combination of the constant velocity and a scan, typically a raster scan at right angles to the constant velocity, so that each spot irradiates an approximately equal-sized rectangular block of the surface. The set of blocks is contiguous and completely cover an initial region of the surface. Once the set of blocks has been scanned, the array constant velocity is halted, and the array of spots is repositioned in a direction opposite to the direction of the surface constant velocity. The array then moves with the combination motion to irradiate a new region of the surface, with a new set of blocks. The size of the repositioning is set so that the new region scanned is contiguous with the initial region. Alternatively, there may be a small region of overlap between the initial region and the new region.

The repositioning is performed substantially instantaneously, and the process of repositioning is herein also termed jumping. The process of scanning and jumping continues until the swathe is completely scanned. The combination of scanning then jumping in a direction opposite to the velocity of the surface ensures that the spots are maintained within the optimal focusing region.

In an alternative embodiment, the surface moves with the constant velocity, and the array of spots is moved with a combination of the constant velocity and scan at right angles to the constant velocity, so that each spot irradiates an approximately equal-sized rectangular sub-block of the surface. The sub-blocks in a first set of sub-blocks are not contiguous and incompletely cover the initial region. Once a first set of sub-blocks has been scanned, the array of spots makes a "sub-jump," in a direction having a component opposite to the direction of the surface constant velocity, and scans a second, different, set of sub-blocks. The process of "sub-jumping" and scanning of sets of sub-blocks is repeated, and the size and direction of the sub-jumps are chosen so that the sets of sub-blocks become contiguous and completely fill the swathe. Using sub-jumps of a relatively small magnitude allows the array of spots to be close in size to the size of the optimal focusing region.

In some embodiments, the surface is a semiconductor wafer surface having a multiplicity of dies. The size of the array of spots may be set, by changing the magnification of a system focusing the beams to the spots, so that corresponding points of dies, lying within the swathe being scanned, are irradiated by the same spots. Alternatively or additionally, for embodiments using sub-jumps, the size of the component of the sub-jump opposite to the direction of the surface constant velocity may be varied, typically between two values. Such a variation may be chosen so that corresponding points of the dies are irradiated by the same spots, so that scanning results, such as die-to-die comparisons, are facilitated.

The present invention will be more fully understood from the following detailed description of the embodiments thereof, taken together with the drawings, a brief description of which follows.

BRIEF DESCRIPTION OF THE DRAWINGS

FIGS. 2A and 2B are schematic diagrams illustrating focused spots in a region being scanned, according to an embodiment of the present invention;

DETAILED DESCRIPTION OF EMBODIMENTS

Embodiments of the present invention focus an array of beams to an array of respective spots on a surface, and relate to methods for scanning the spots over the surface. Substantially any type of beam, i.e., beams of particles, or beams of waves, may be used. As one example, the beams may be charged particle beams, the charged particles being positive or negative ions or electrons. In an alternative example, the beams may consist of electromagnetic waves from substantially any part of the electromagnetic spectrum, such as waves in the visible, near-visible, and/or X-ray regions of the spectrum.

Figure 1A:
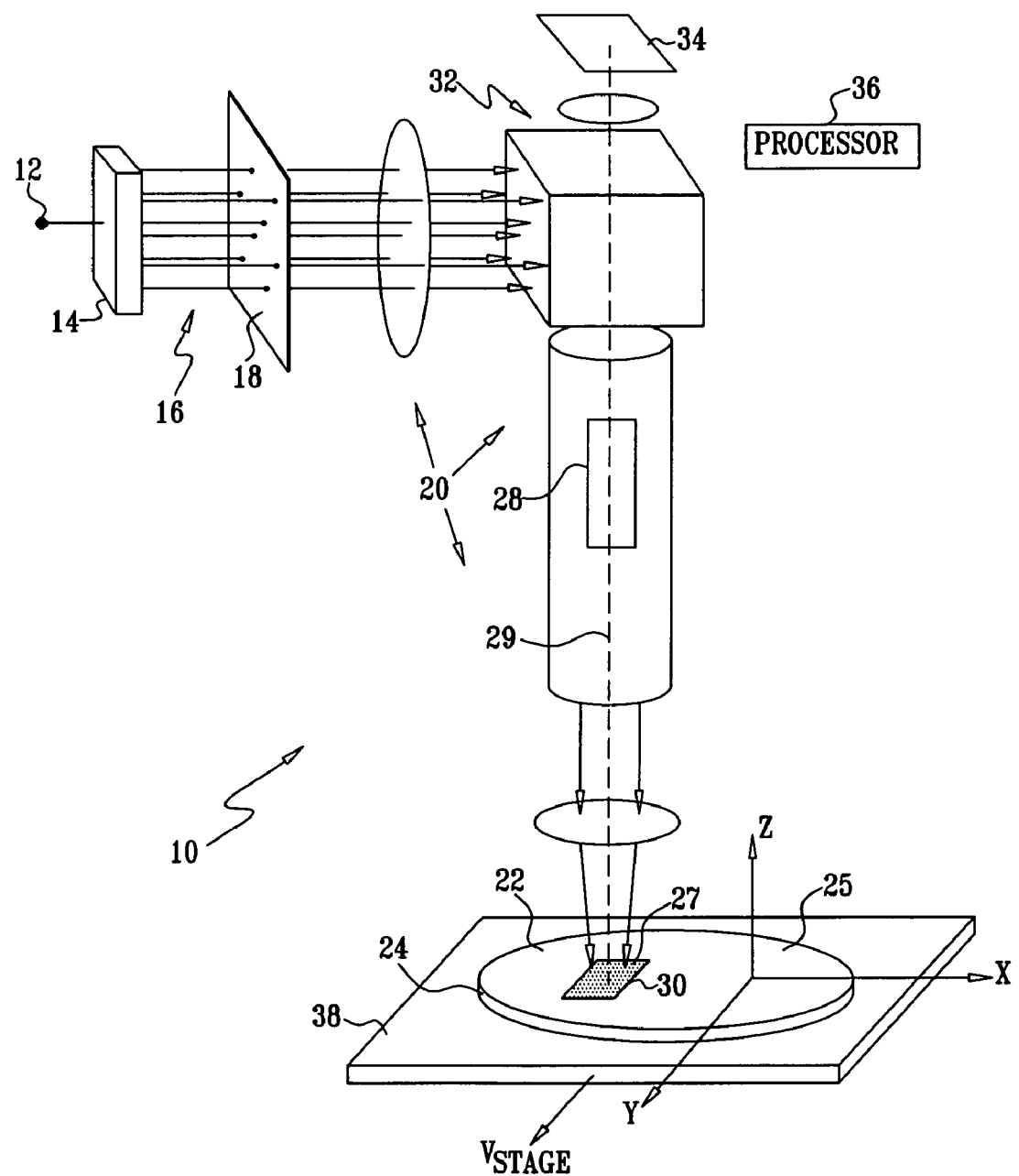
FIGS. 1A and 1B are schematic illustrations of inspection apparatus, according to an embodiment of the present invention.

Reference is now made to FIG. 1A, which is a schematic illustration of an optical inspection apparatus 10, according to an embodiment of the present invention. Apparatus 10 has a light source 12, typically a laser source, which is divided by a beam multiplexer 14 into an array 16 of generally parallel beams. Typically, a cross-section 18 of array 16 is symmetrical. Herein, by way of example, cross-section 18 is assumed to have six-fold symmetry, i.e., nearest neighbors of elements of the cross-section are at the vertices of equilateral triangles. However, it will be understood that cross-section 18 may have any other convenient form of symmetry, such as two-, three-, or four-fold symmetry. It will also be understood that any other convenient system, such as a multiplicity of generally similar beam sources, may be used to generate array 16, and that all such systems are assumed to be comprised within the scope of the present invention. A processor 36 operates the elements of apparatus 10.

Objective optics 20 direct and focus beam array 16 onto a plane surface 22 of an element 24, producing an array of focused spots 27 on the plane surface of the element. Element 24 is mounted on a motion stage 38. Surface 22 is assumed to contain orthogonal x and y axes, and to be normal to a z axis. Processor 36 is able to operate stage 38 so that surface 22 translates in an x and/or a y direction, or in any combination of these directions. Optics 20 comprise a scanner 28, which is operated by processor 36 to scan focused spots 27 across surface 22. Systems corresponding to optics 20 and scanner 28 are well known in the art, the latter typically comprising a mirror and/or acousto-optic elements for diverting beams 16. Thus optics 20 and scanner 28 may be implemented from substantially any elements which are able to focus beams 16 onto respective portions of surface 22, and to scan the focused beams across the surface. Objective optics 20 may typically also be at least partly utilized as imaging optics 32, the imaging optics forming images of respective spots 27 onto a detector array 34. Signals from array 34 are processed by processor 36.

While scanner 28 is typically able to scan beam array 16 so that spots array 27 moves across relatively large areas of surface 22, in practice there is an aberration-corrected region 30 within which the focused spots may be brought to an optimal focus, and outside of which the focused spots are less than optimally focused. Region 30 is typically an approximately oval region, approximately symmetrically located with respect to an optical axis 29 of apparatus 10. Region 30 is herein assumed to be contained within an approximately square region of side 500 μm. In embodiments of the present invention, scanner 28 maintains focused spot array 27 substantially within aberration-corrected region 30.

Figure 1B:
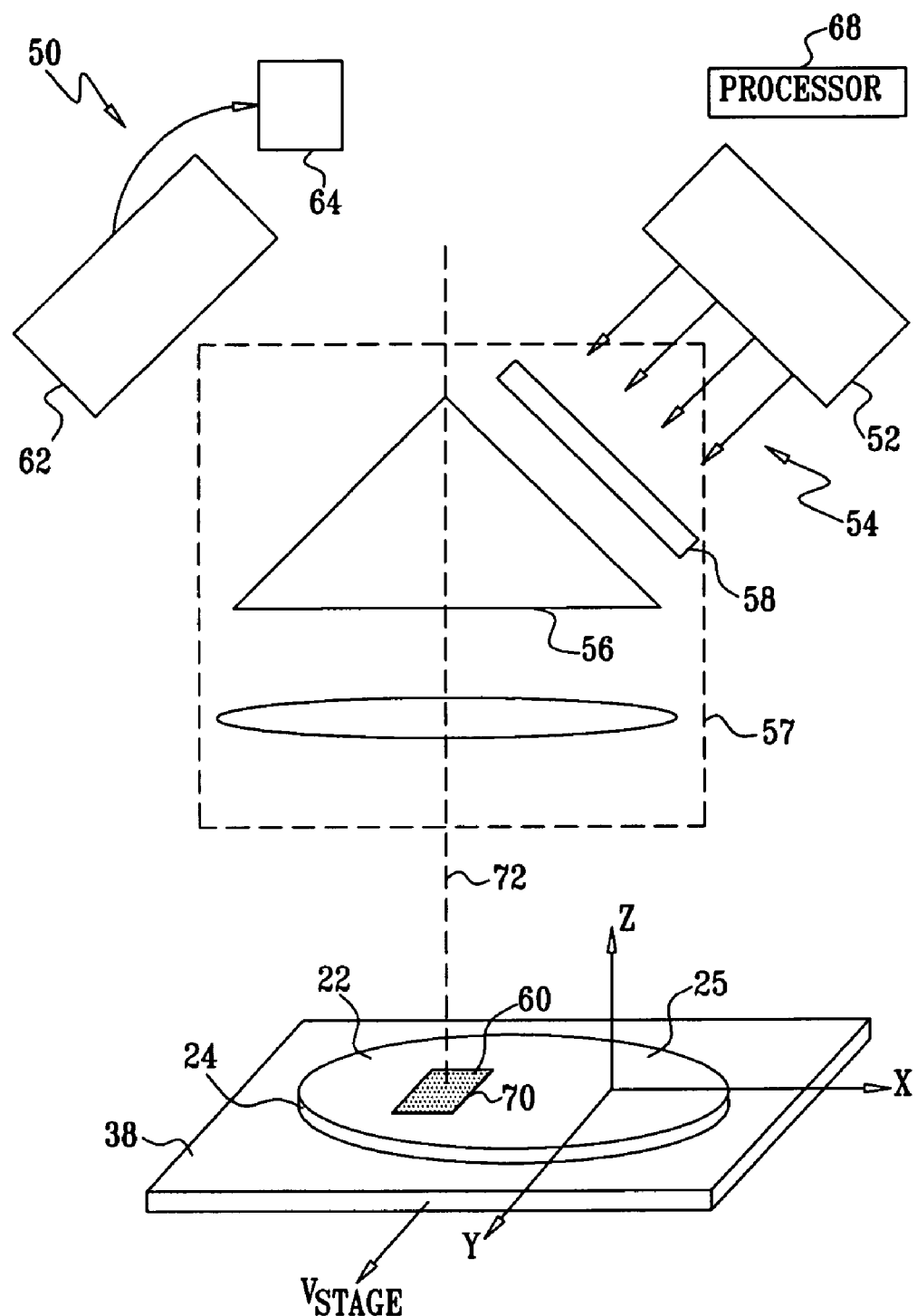

Reference is also made to FIG. 1B, which is a schematic illustration of a charged particle inspection apparatus 50, according to an embodiment of the present invention. Apparatus 50 may also be used to inspect element 24, which as for apparatus 10, is assumed to be mounted on stage 38. Apparatus 50 comprises a charged particle source 52, herein assumed by way of example to be an electron source, which generates an ordered array of charged particle beams 54. Beams 54 pass through a scanner 58 and a beam splitter 56, comprised in electron optics 57, so as to create a focused spot array 60 on surface 22. Spot array 60 is assumed to be generally similar to array 27. A detector 62 collects secondary electrons (SE) or backscattered electrons (BE), which are directed to the detector by beam splitter 56. An imager 64 receives signals from detector 62, and in response generates an SE or a BE image of surface 22. Elements of apparatus 50 are operated by a processor 68.

As for apparatus 10, while scanner 58 is typically able to scan focused spot array 60 so that the spots move across relatively large areas of surface 22, in practice there is an aberration-corrected region 70 within which the focused spots may be brought to an optimal focus, and outside of which the focused spots are less than optimally focused. Region 70 typically has properties generally similar to those described above for region 30, and is herein assumed to be approximately symmetrically located with respect to an axis 72 of optics 57. In embodiments of the present invention, scanner 58 maintains focused spot array 60 substantially within aberration-corrected region 70.

Apparatus 10 and apparatus 50 may be used, inter alia, for inspection and/or for photolithography of wafers and/or reticles. Hereinbelow, by way of example, it is assumed that element 24 comprises a semiconductor wafer having a plurality of substantially identical dies 25, and that apparatus 10 or apparatus 50 is used to inspect surface 22 of the wafer.

The following description is generally drawn to embodiments wherein the beams are generated using a particular type of electromagnetic wave, using optical inspection apparatus 10. It will be appreciated that this is by way of example, and those skilled in the art will be able to adapt the description to spots produced by any type of wave beam. It will also be appreciated that those skilled in the art will be able to adapt the description, mutatis mutandis, to inspection by substantially any type of particle beam apparatus, such as charged particle inspection apparatus 50.

Figure 1C:
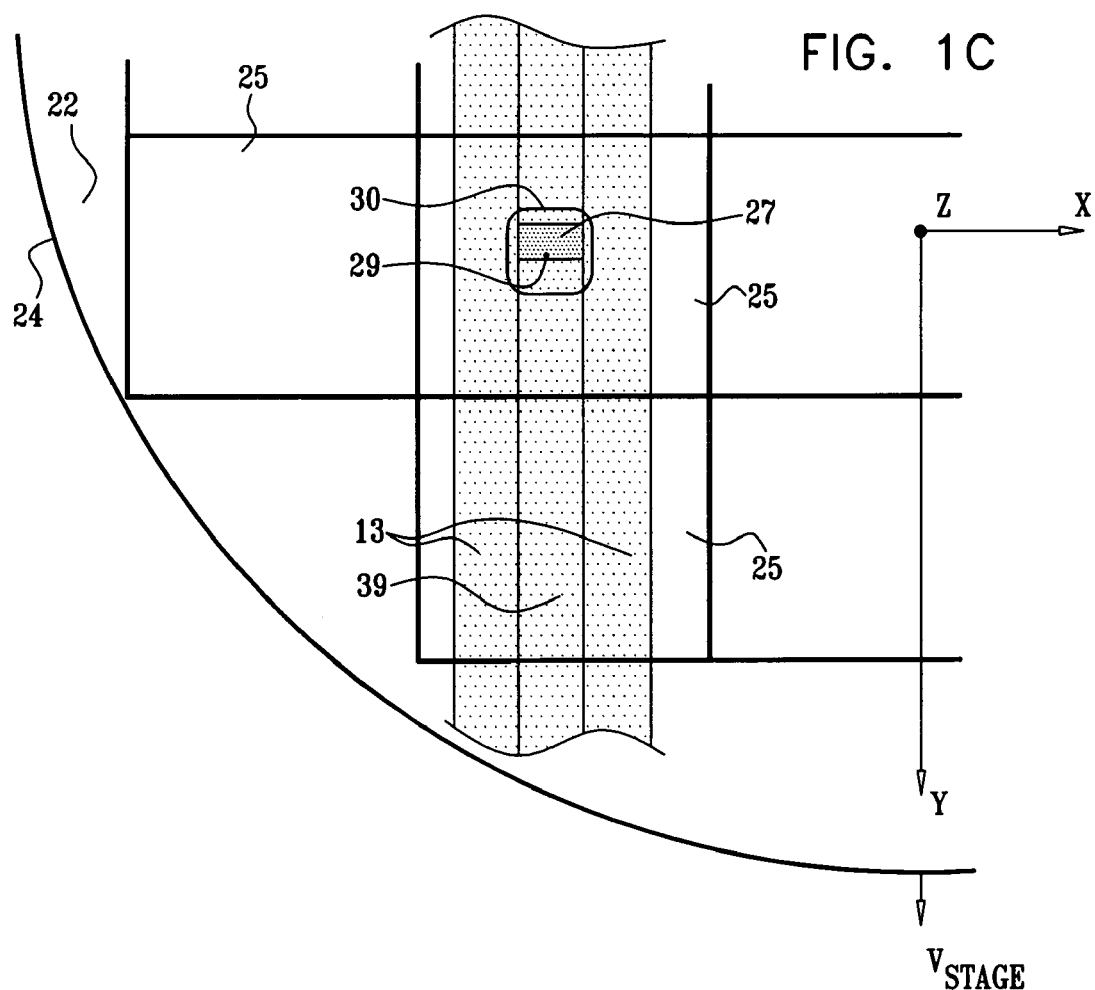
FIG. 1C is an enlargement of a section of FIG. 1A, according to an embodiment of the present invention.

FIG. 1C is an enlargement of a section of FIG. 1A, showing region 30, array 27, and dies 25 in more detail, according to an embodiment of the present invention. As is described in more detail below, processor 36 operates stage 38 and scanner 28 of apparatus 10 so that a swathe 39 is scanned across surface 22, and typically so that other swathes 13 are also scanned across the surface.

Figure 2A:
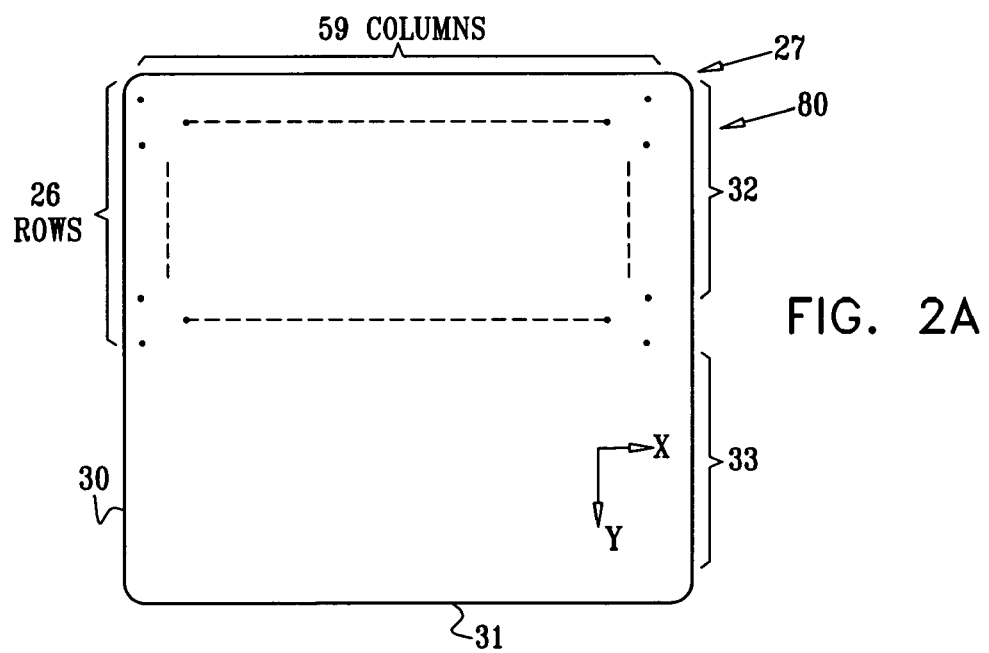

FIGS. 2A and 2B are schematic diagrams illustrating focused spots 27 in region 30, according to an embodiment of the present invention. In this embodiment, spots 27 are formed as 59 columns of 26 rows of spots, so that there are a total of 1534 spots, formed from a corresponding 1534 beams generated by multiplexer 14. The columns of spots define a beam array axis, and may be set to be parallel to the y axis. Each of the spots is assumed to be equidistant from its nearest neighbors, the distance being 10 µm. It will be appreciated that the above numerical values and orientation for spots 27 are provided by way of example, and that embodiments of the present invention may use substantially any convenient number, separation, and orientation of the spots. By way of example, a different number of spots is used, in an array generally similar in form to that described herein with respect to FIGS. 2A and 2B, in an alternative embodiment described with reference to FIGS. 4-6.

Spots 27 are initially positioned to be in an upper portion 32 of region 30. In the description herein, unless otherwise stated, terms such as "upper," "lower," and "left-side," when used in relation to spots 27, are used to clarify the description, and refer to positions within FIGS. 2A and 2B and other figures herein, not to an aspect of apparatus 10. In operating apparatus 10, surface 22 (FIGS. 1A and 1C) is moved at a constant velocity $V_{stage}$ in the y direction, so that the surface translates relative to axis 29. During a first part of scanning of spot array 27, the array moves with two components which are added vectorially: a component $V_{stage}$, and a raster scan 80 component. An enlarged section I of raster scan 80 is shown in FIG. 2B, and in enlarged section I, individual spots of array 27 are labeled A1, A2, . . . , B1, B2, . . . , where A, B, . . . are column labels, and 1, 2, . . . are row labels. Enlarged section I illustrates the raster pattern of spots 27 due to raster scan 80 alone, and corresponds to the motion of the spots as seen by an imaginary observer on moving surface 22. Processor 36 sets the raster scan so that each spot of array 27 scans a substantially similar 10 µm×8.66 µm rectangle 82, by scanning a predetermined number of rows within the rectangle that are perpendicular to the y-direction. As described further below, the actual number of rows scanned depends on a size of scanned pixels in rectangle 82

Rectangles 82, generated by the raster scan, are contiguous and are arranged so that there are no gaps between rectangles. At the conclusion of the raster scan, spot A1 will be at a point 84, and an approximately rectangular region 86 of surface 22, shown in more detail in section II of FIG. 2B, will have been scanned by array 27. Region 86 is enclosed by two vertical sides 90 having lengths of 26×10 µm=260 µm, and two horizontal crenellated sides 88 and 92, having lengths of 59×0.866×10 µm=511 µm. Thus region 86 has approximate dimensions of:

$$FOV_y \times FOV_x = 260 \text{ µm} \times 511 \text{ µm} \quad (1)$$

where $FOV_y$ is the y Field of View value of the scanned region, and $FOV_x$ is the x Field of View value of the scanned region.

It will be understood that so long as the array is moved with the same component $V_{stage}$ as the stage, the dimensions $FOV_y$, $FOV_x$ of region 86 do not depend on the value of $V_{stage}$.

Depending on the value of $V_{stage}$, the position of array 27 will have moved from its initial upper portion 32. (If $V_{stage}=0$, the only movement of the array is because of the raster scan, and the position of array 27 remains substantially in upper portion 32.) Processor 36 sets the value of $V_{stage}$ so that at the conclusion of the raster scan, bottom line 88 of region 86 is approximately coincident with a bottom line 31 of region 30 (FIG. 2A). In other words, during one scan, processor 36 moves array 27 from upper portion 32 to a lower portion 33 of region 30. As described in more detail below with reference to FIG. 3, at conclusion of the raster scan, processor 36 repositions array 27 back to its initial position in upper portion 32, and the processor then repeats the raster scan, while continuing to move the array and surface 22 with velocities $V_{stage}$. The process of moving array 27 with a combination of raster scanning and velocity $V_{stage}$ while moving surface 22 with velocity $V_{stage}$, then repositioning the array back to its initial position, continues iteratively until a complete swathe 39 (FIG. 1C) has been scanned on surface 22.

The speed of the repositioning described herein, compared to the velocity $V_{stage}$, is typically extremely high, so that the repositioning is essentially instantaneous. Typically, the time taken to reposition the array is less than 1% of the time for the array to scan. The time for the array to scan, T, is described in relation to FIG. 3 and also in relation to expression (3) below. Herein the term "jump" is also used to describe the repositioning that is implemented.

Figure 3:
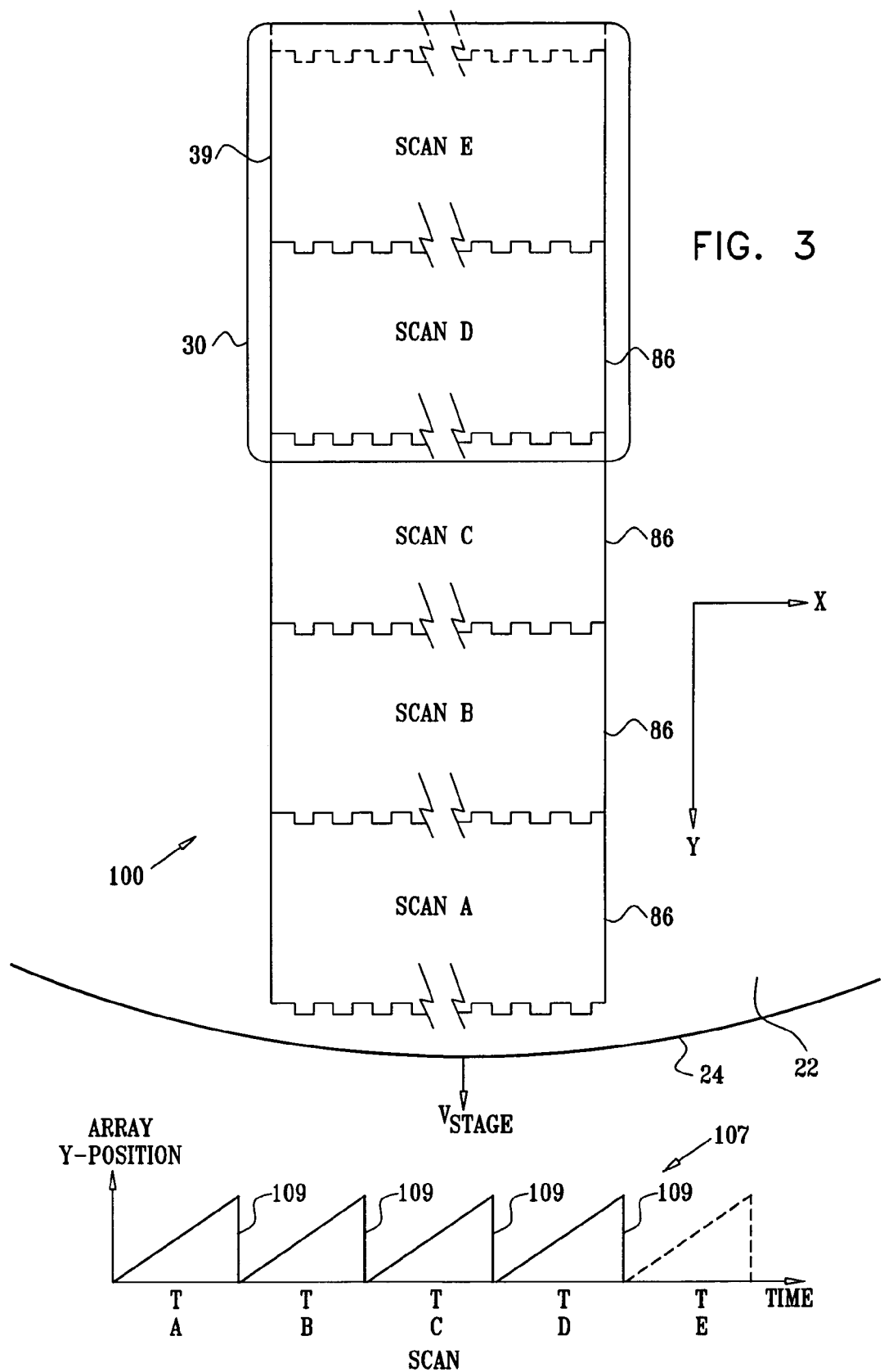
FIG. 3 shows a snapshot after a number of raster scans have been performed by the apparatus of FIGS. 1A or 1B, according to an embodiment of the present invention.

FIG. 3 shows a schematic "snapshot" 100 after a number of the scans of swathe 39 have been performed, as described above, according to an embodiment of the present invention. By way of example, four scans of substantially identical regions 86 of swathe 39 are assumed to have completed, and are shown in FIG. 3 as scans A, B, C, and D. Scan A is the first scan, and the most recent scan, scan D, is assumed to have just completed, so that apparatus 10 is about to begin a scan E. The position of region 30 is also shown in snapshot 100. After each scan A, B, . . . , processor 36 repositions the array in the negative y direction, by an amount that typically makes adjacent rectangles 86 contiguous with each other. In some embodiments of the present invention, processor 36 repositions the array so that there is a small overlap between adjacent rectangles 86.

Regardless of whether or not there is overlap between adjacent rectangles, a graph 107 of the y-position of array 27 vs. time is a saw-tooth graph, with the vertical lines 109 of the graph corresponding to the jumps applied to the array. T corresponds to the time for processor 36 to perform one scan of array 27, time T being equal to the time taken to scan one rectangle 82 (FIGS. 2A and 2B).

Typically, the value of T depends on the time taken by processor 36 to scan an individual pixel on surface 22, and on the number of pixels scanned by each spot of array 27. The latter also affects the number of rows scanned within each rectangle 82. Thus, if an individual pixel is square with a side p µm, the number of pixels $N_{pix}$, and the number of rows R, scanned within a specific rectangle 82, are given by expression (2):

$$N_{pix} = \frac{86.6}{p^2} \quad (2)$$

$$R = \frac{10}{p}$$

If processor 36 takes a time $T_p$ to scan a pixel, then the time T that the processor needs to scan a complete rectangle 82 is given by expression (3):

$$T = N_{pix} \cdot T_p = \frac{86.6}{p^2} \cdot T_p \quad (3)$$

Processor 36 uses the value of T from expression (3) to adjust the value of $V_{stage}$ so that scans such as scan A and scan B (FIG. 3) are contiguous or slightly overlapping. After each time T, processor 36 repositions array 27 to irradiate a new region of surface 22. Using the values for array 27 given above, in the case of no overlap, processor 36 repositions array 27 260 µm in the negative y-direction after each scan has completed. The value of 260 µm corresponds to the y height of the 26 rows scanned by array 27. For an overlap between scans of 10 µm, corresponding to the height of one rectangle 82, processor 36 repositions the array by 250 µm in the negative y-direction after each scan has completed. In either case, the value of $V_{stage}$ is given by expression (4):

$$V_{stage} = \frac{FOV_y}{T} \qquad (4)$$

To account for a reposition time, i.e., a jump time, such as is described above, the value of $V_{stage}$ given by expression (4) (and also that given by expression (8) below) may be reduced correspondingly, as will be apparent to those skilled in the art.

It will be appreciated that during the whole time that array 27 is operated, and as is illustrated in FIG. 3 for scans D and E, the focused beam of the array remains within region 30.

It will also be appreciated that swathe 39 is formed of contiguous or slightly overlapping regions 86, each one of which scans a portion of surface 22 with substantially no un-scanned parts within the regions. To scan the whole of surface 22, apparatus 10 typically scans multiple swathes, each swathe either being contiguous with each other, or slightly overlapping. For example, one or more second swathes 13 (FIG. 1C), adjacent to swathe 39, may be 511 µm from swathe 39, measured along the x-axis, giving no overlap, or may be 502 µm along the x-axis from swathe 39, giving an overlap of one rectangle 82.

It will be appreciated that, in contrast with other scanning processes known in the art, the relative beam positions of the spots generated by array 27 in the process described herein with reference to FIGS. 2A, 2B and 3 do not need to be very accurate. In particular, the process described herein is completely unaffected by any misalignment between the direction of travel of stage 38 and the direction of the columns of array 27.

As stated above, embodiments of the present invention described with reference to FIGS. 2A, 2B, and 3 provide a set of regions 86, each of the regions having substantially no un-scanned parts. After each region 86 is scanned, array 27 is repositioned. Swathe 39 is then formed by "joining" adjacent regions 86 together. In an alternative embodiment described below with reference to FIGS. 4-6, the same general pattern of scanning, repositioning the array in the negative y-direction, then scanning, is followed. Also, as in the embodiments described above, surface 22 and array 27 are both moved with a y-velocity $V_{stage}$, the array also having a scan imposed on its $V_{stage}$ motion. However, in contrast to the system described above, each specific scan of the alternative embodiment does have un-scanned regions. As is described below, the scans with un-scanned regions are combined together, and the combination eliminates the un-scanned regions.

Figure 4:
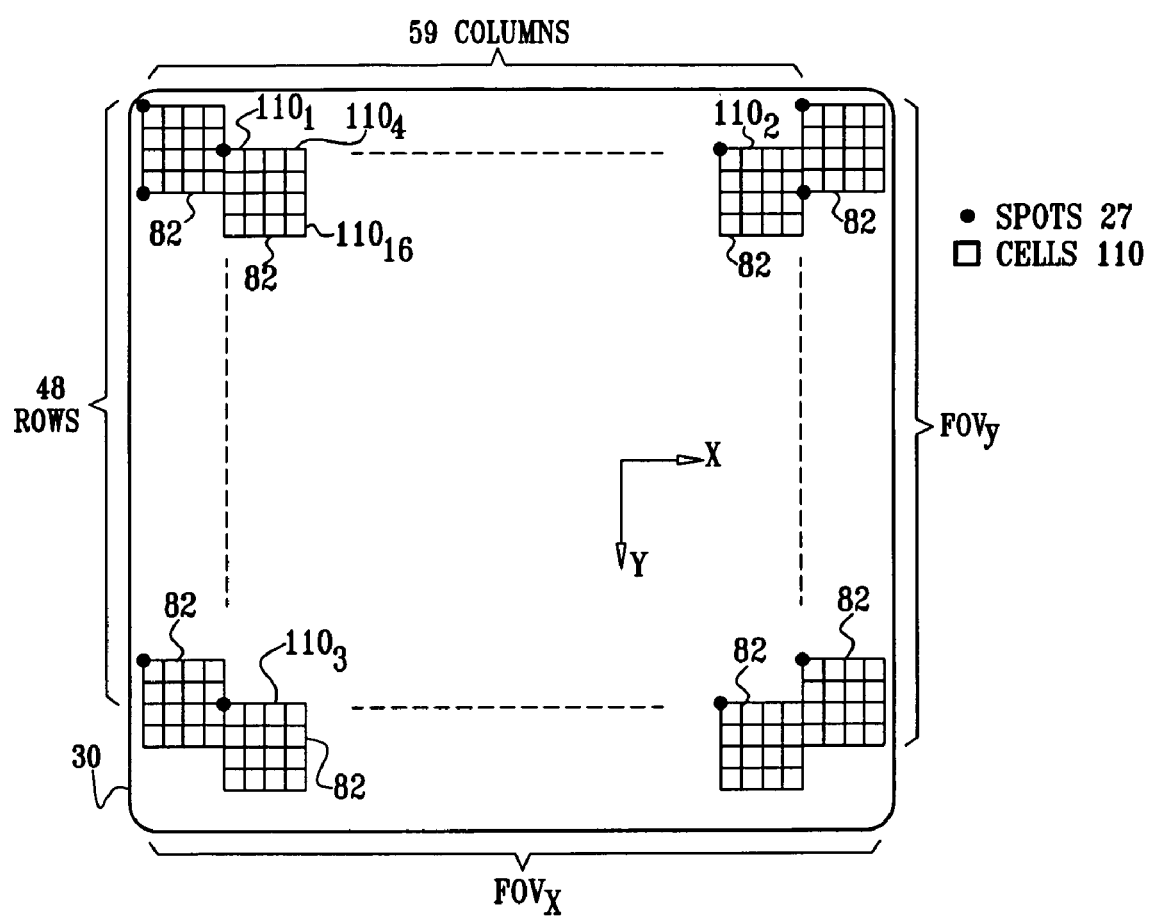
FIG. 4 is a schematic diagram illustrating focused spots in a region being scanned, according to an alternative embodiment of the present invention.

FIG. 4 is a schematic diagram illustrating focused spots 27 in region 30, according to an alternative embodiment of the present invention. In the alternative embodiment, spots 27 are formed as 59 columns of 48 rows of spots, so that there are a total of 2832 spots, formed from a corresponding 2832 beams generated by multiplexer 14. The columns of spots are set to be parallel to the y axis. Each of the spots is assumed to be equidistant to its nearest neighbors, the distance being 10 µm, so that each spot defines contiguous rectangles 82 having dimensions 10 µm×8.66 µm, as described above with reference to FIGS. 2A and 2B. As shown in FIG. 4, unlike the embodiment described with reference to FIGS. 2A, 2B, and 3, the 2832 spots substantially completely fill region 30. Using the definitions for $FOV_y$ and $FOV_x$ given above in expression (1), the values for $FOV_y$ and $FOV_x$ are respectively 480 µm and 511 µm.

If the scanning system described above with reference to FIGS. 2A, 2B, and 3 is applied to the array of FIG. 4, i.e., if surface 22 is moved with a velocity $V_{stage}$ and array 27 moves for a time T with a combination of $V_{stage}$ and a raster scan, at the end of each scan approximately half of the array will be outside region 30.

To avoid this situation, some embodiments of the present invention may use smaller reposition values, or jumps, than the size of the jumps described above with reference to FIGS. 2A, 2B, and 3. These smaller jumps are referred to herein as "sub-jumps," and the time difference between sub-jumps is reduced from the time T described above. Each rectangle 82 is divided into a number of generally similar cells 110. A respective cell 110 of every rectangle 82 is scanned using substantially the same method as described above for the embodiment of FIG. 2, i.e., surface 22 is moved with velocity $V_{stage}$, and array 27 is moved with a combination of the same velocity $V_{stage}$ and a raster scan that scans the specific cell. At the conclusion of the cell raster scan, array 27 makes a sub-jump in the negative y-direction and another respective cell 110 of every rectangle 82 is scanned. The process of cell scanning and making sub-jumps in the negative y-direction continues. During an initial phase of the process, only some of the cells of rectangles 82 are scanned. Once the initial phase has completed, all the cells of the rectangles are scanned, so that continuing the process after the initial phase ensures that further rectangles 82 are completely scanned. The process for using the sub-jumps is described in more detail hereinbelow.

In each rectangle 82 there are assumed to be an integral number J of cells 110. The value of J is related to the number M of rows of array 27 according to expression (5):

$$J = \frac{M}{I} \qquad (5)$$

where I is a positive integer less than M.

The number of pixels $N_{pixc}$ in each cell 110, and the time $T_c$ needed to scan each cell, are given by expressions (6) and (7), respectively derived from expressions (2) and (3) above.

$$N_{pixc} = \frac{86.6}{J \cdot p^2} \qquad (6)$$

$$T_c = N_{pixc} \cdot T_p = \frac{86.6}{J \cdot p^2} \cdot T_p \qquad (7)$$

The relation between $FOV_y$ and $V_{stage}$ is given by expression (8), derived from expression (4) above.

$$V_{stage} = \frac{FOV_y}{J \cdot T_c} \qquad (8)$$

After each time $T_c$, i.e., after a cell 110 has been scanned, array 27 makes a sub-jump in the negative y-direction given by expression (9):

$$Subjump = \frac{FOV_y}{J} \quad (9)$$

By way of example, I is assumed to be 3, so that from expression (5) J=16, and each rectangle 82 is divided into 16 respective cells 110, identified herein as cells $110_1$, $110_2$, ... $110_{16}$, as shown in FIG. 4. Herein cells 110 of rectangle 82 are assumed to be formed as a 4×4 array, but it will be appreciated that any other convenient array of 16 cells, such as a 2×8 array, may be used. As stated above, the value of $FOV_y$ is 480 μm, so that from expression (9) the value of the sub-jump is 30 μm.

In the initial scanning phase a first set of cells, e.g. cells $110_1$, is scanned, taking a time $T_c$ for the scan, after which array 27 makes the sub-jump, and a different set of cells, e.g., cells $110_3$, is scanned. The process of scanning then sub-jumping continues. In the initial scanning phase some of cells 110 of rectangles 82 are not scanned; once the initial scanning phase has completed, all cells 110 of every rectangle 82 are scanned.

Figure 5:
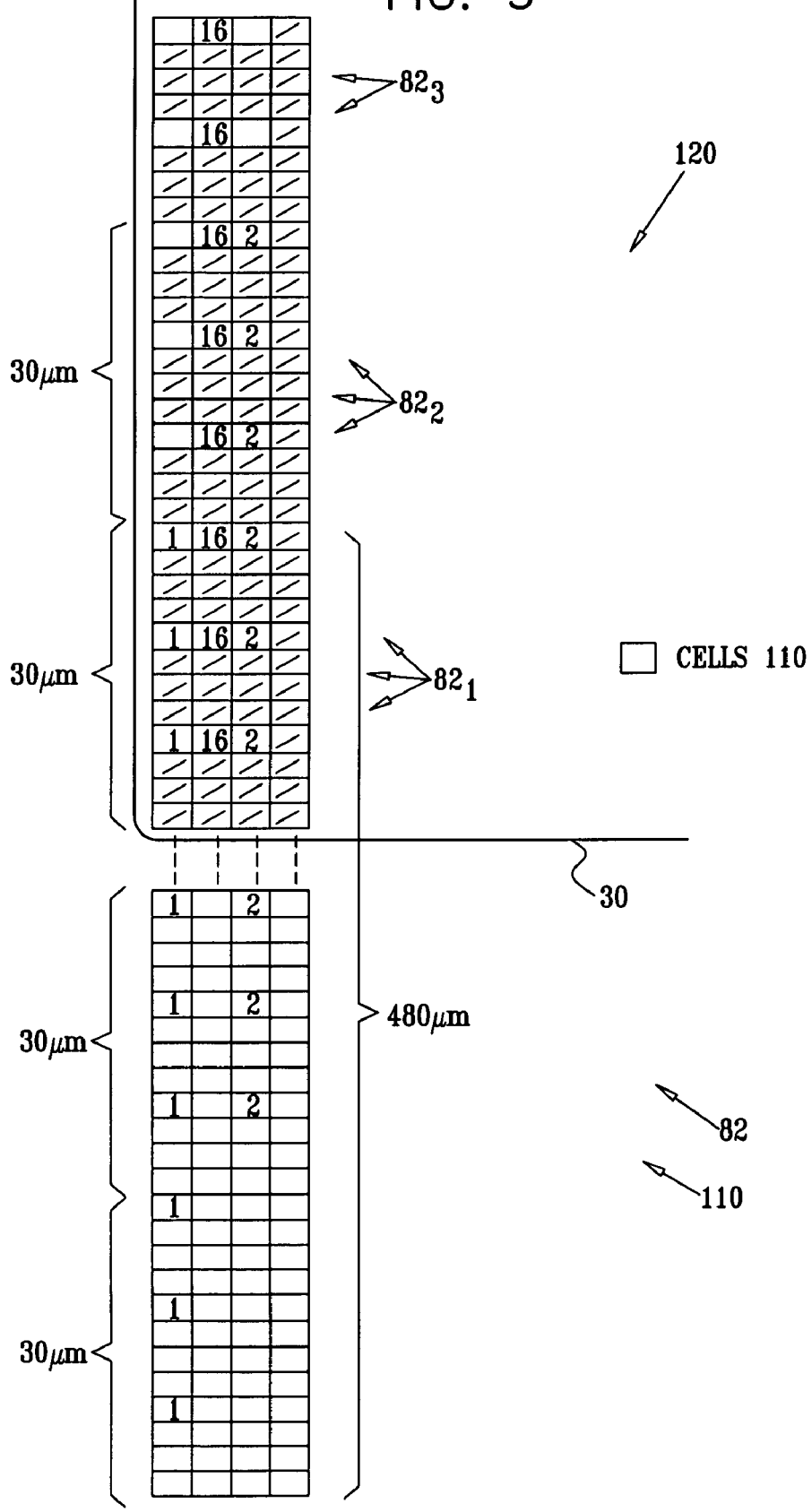
FIG. 5 is a diagram showing a snapshot of cells scanned by an array of the apparatus of FIGS. 1A or 1B, according to the alternative embodiment of the present invention.

FIG. 5 is a diagram showing a snapshot 120 of cells 110 scanned by array 27, according to the alternative embodiment of the present invention. Snapshot 120 is of the left-hand set of rectangles 82 of array 27 in FIG. 4, and is shown after 15 sub-jumps have been made, so that 16 scans of array 27 have been made, a 16$^{th}$ sub-jump is about to be made, and a 17$^{th}$ scan is about to start. Snapshot 120 also shows a lower left margin of region 30. In the example described herein, cells that have been scanned during a first scan are labeled with "1", cells scanned during a second scan are labeled with "2", ..., and cells scanned during a 16$^{th}$ scan are labeled with "16." Other scanned cells are labeled with "/," and cells that have not been scanned are empty.

Snapshot 120 illustrates that after a first scan of cells $110_1$, a sub-jump of 30 μm in the negative y-direction is made, and a second scan of cells $110_3$ is made. For the 16$^{th}$ scan, cells $110_2$ are scanned, and once this scan has completed, all cells of the three sets of rectangles 82 closest to the lower edge of region 30, labeled $82_1$, have been scanned. For the 17$^{th}$ scan, the process begins to repeat, i.e., un-scanned cells $110_1$ are scanned, and during this scan, the $V_{stage}$ component applied to array 27 moves the three sets of rectangles $82_2$ to the lower edge of region 30. At completion of the 17$^{th}$ scan rectangles $82_2$ will also have been completely scanned. Similarly, at completion of the 18$^{th}$ scan rectangles $82_3$ will be closest to the lower edge of region 30, and will have been completely scanned.

Figure 6:
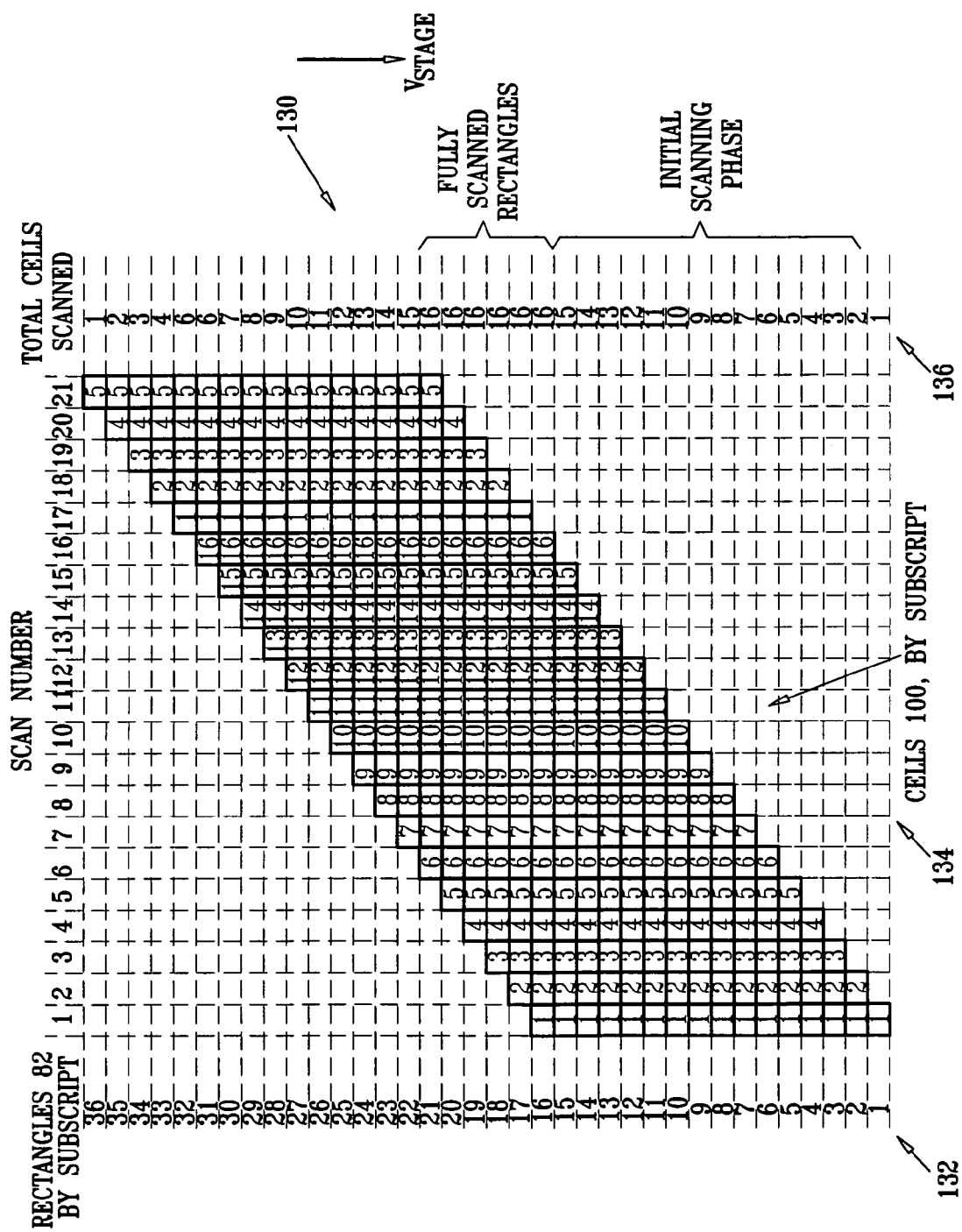
FIG. 6 is a diagram showing parameters of scanned rectangles after a number of scans of the apparatus of FIGS. 1A or 1B have been made, according to the alternative embodiment of the present invention.

FIG. 6 is a diagram 130 showing parameters of scanned rectangles 82 after 21 scans have been made, according to the alternative embodiment of the present invention. After each scan a sub-jump equal to the y-height of three rectangles 82 is made. In diagram 130, a column 132 refers to the set of rectangles $82_1$, ... by the subscript of the rectangles, and it will be understood that each set comprises three rectangles 82. In diagram 130 it is assumed that in the first scan cells $110_1$ are scanned, in the second scan cells $110_2$ are scanned, ..., and in the 16$^{th}$ scan, cells $110_{16}$ are scanned. A region 134 of the diagram shows cells scanned during each scan; in the region the cells are referred to by their subscripts.

As shown by a column 136, and as has also been described above with reference to FIG. 5, after an initial scanning phase of 15 scans, all 16 cells of rectangles 82 begin to be scanned. Thus, for scans 16-21, complete rectangles 82 are scanned.

It will be appreciated that the process described above with reference to FIGS. 4-6 may be applied to completely scan a swathe 39 of surface 22, substantially regardless of the length of the swathe. Typically, in order to completely scan the beginning of the swathe, the initial scanning phase is started before region 30 completely covers surface 22, so that complete scanning of rectangles 82 begins as region 30 does completely cover surface 22.

It will also be appreciated that for the process described with reference to FIGS. 4-6 the relative beam positions of the spots generated by array 27 do not need to be very accurate, and that any inaccuracies may be taken care of by including a small overlap between cells 110. Furthermore, because of the small sub-jump size, the value of $FOV_y$ for array 27 may be set to be nearly equal to the y-value of aberration-corrected region 30.

Figure 7:
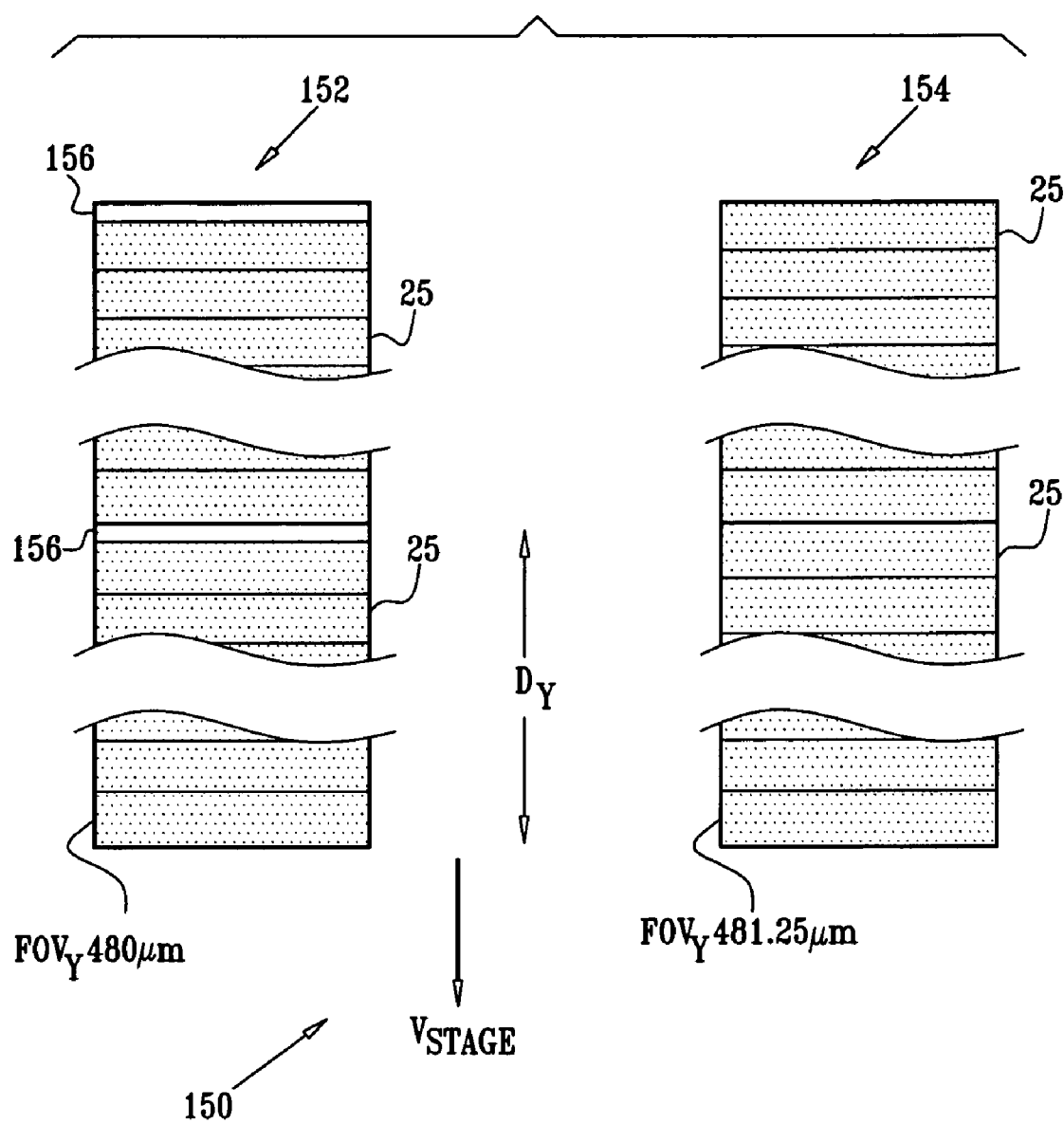
FIG. 7 is a diagram showing a relation between a scanned field of view and dimensions of dies being scanned, according to an embodiment of the present invention.

FIG. 7 is a diagram 150 showing a relation between the scanned $FOV_y$ and the dimensions of dies 25, according to an embodiment of the present invention. Typically, dies 25 of surface 22 (FIG. 1C) are rectangular with substantially identical external dimensions. In a number of applications of the scans described herein it will be appreciated that it is advantageous that identical locations within respective dies are scanned by the same spot of array 27, and that the locations when scanned have the same offset with respect to optical axis 29. This condition is herein termed "die periodicity." It will be understood that maintaining die periodicity facilitates die-to-die comparisons; other applications where maintaining die periodicity is advantageous will be apparent to those skilled in the art. If the y-dimension of each die 25 is $D_y$, then identical locations of dies will be scanned by the same spot of array 27, i.e., die periodicity holds, when an integral number of scans exactly fill the die, corresponding to expression (10) being true:

$$FOV_y = \frac{D_y}{I} \quad (10)$$

where I is a positive integer.

For example, if $D_y$ is 15.4 mm (15,400 μm), and $FOV_y$ is 480 μm, as in the example above, then expression (10) is not true, as is illustrated by section 152 of diagram 150. In section 152 each die 25 has an unscanned region 156, and die periodicity does not hold. To cause die periodicity to hold, a relatively small change of magnification of array 27 may be made, changing the value of $FOV_y$ so that expression (10) is true. For example, if $FOV_y$ is changed to 481.25 μm, then $$481.25 = \frac{15,400}{32},$$

and die periodicity holds, as is illustrated by section 154 of the diagram.

Figure 8:
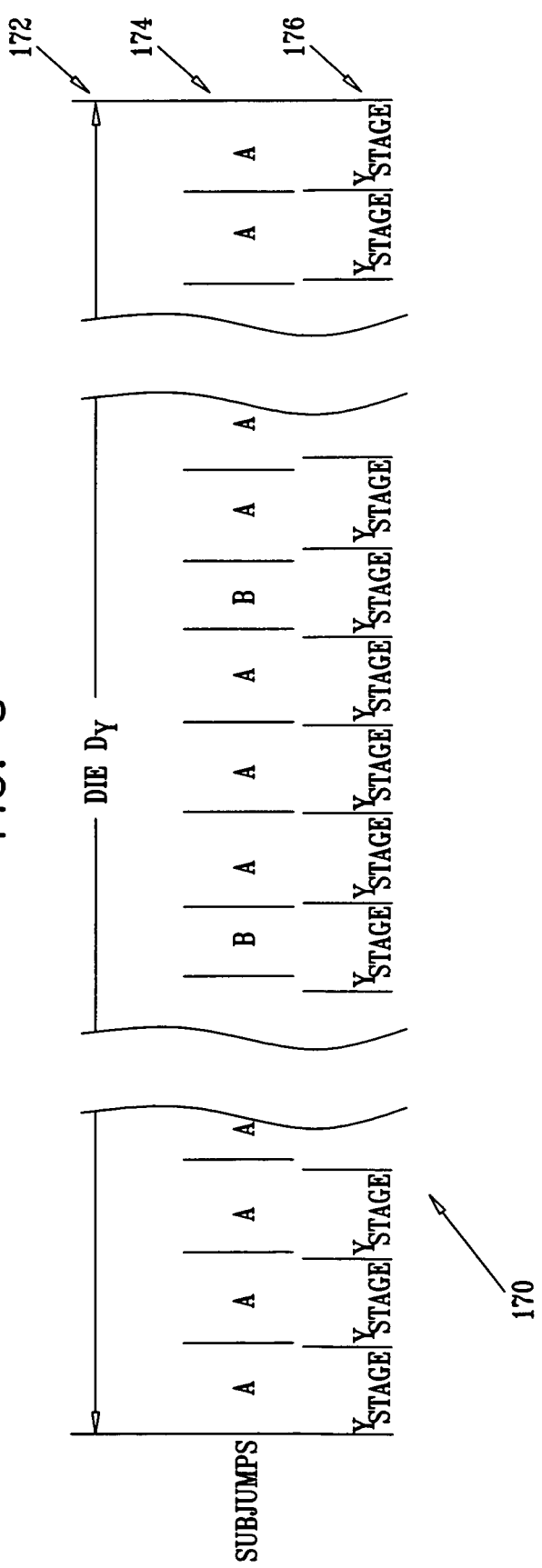
FIG. 8 is a diagram illustrating a method for maintaining die periodicity, according to an embodiment of the present invention.

FIG. 8 is a diagram 170 illustrating an alternative method for maintaining die periodicity, according to an embodiment of the present invention. In order to maintain die periodicity for the embodiment described above with respect to FIGS. 4-6, processor 36 applies two different sized sub-jumps to array 27, as shown in a row 174, wherein "A" indicates a sub-jump of one size and "B" indicates a sub-jump of a different size. Processor 36 also adjusts the velocity $V_{stage}$ of stage 38 so that the constant distance $Y_{stage}$ traveled by stage 38 during each of the sub-jumps lies between the two sub-jump sizes. The distances $Y_{stage}$ traveled by the stage are shown in a row 176, and processor 36 adjusts their number so that they exactly total a die size $D_y$, shown in row 172. Processor 36 also adjusts the numbers of the two sub-jumps, A, B, so that the total distance traversed by the sub-jumps is exactly equal to $D_y$.

The following description details one method for selecting the size and number of the sub-jumps, and the distance traveled by the stage during each sub-jump, in order to maintain die periodicity. Other methods will be apparent to those having ordinary skill in the art, and all such methods are assumed to be included within the scope of the present invention.

The description uses the following terms:

$D_y$, die size in the y-direction;

Nby, the number of rows of spots in array 27;

pitch, the distance between spots;

Ncell, the number of cells per rectangle 82; and

J, the number of rectangles 82 in the sub-jumps of the embodiment described above with respect to FIGS. 4-6.

J, Nby, and Ncell are related by the expression:

$$Nby = J \cdot Ncell \quad (11)$$

Values of non-negative integers D, E, and F, are selected so that the following expressions are true:

$$D_y = D \cdot pitch + d \, (0 \leq d \leq pitch)$$

$$D = E \cdot Nby - F \, (0 \leq F < NBy) \quad (12)$$

Processor 36 implements $N_J$ sub-jumps of size $Y_J$ and $N_{J-1}$ sub-jumps of size $Y_{J-1}$, where:

$$N_J = (E \cdot Ncell - F), \quad (13)$$
$$Y_J = \frac{J \cdot D_y}{D}$$
$$N_{J-1} = F,$$
$$Y_{J-1} = \frac{(J-1) \cdot D_y}{D}$$

After each sub-jump, processor 36 sets array 27 to scan a different cell, from 1 to Ncell, of rectangles 82, and repeats the scanning sequence.

From expressions (13), the total number of sub-jumps, $N_J + N_{J-1}$, is E·Ncell. Since E is an integer, this is an integral multiple of Ncell, so that each period begins on the same cell as the previous period.

Processor 36 sets the velocity of stage 38, $V_{stage}$, so that between sub-jumps, i.e., during the scanning of each cell, the stage moves in the y-direction by the value given by expression (14) below. Since processor 36 moves array 27 with the same velocity $V_{stage}$ during scanning of the array, array 27 moves in the y-direction by the same amount.

$$Y_{stage} = \frac{D_y}{(N_J + N_{J-1})} \quad (14)$$

Using expressions (13) above, the total distance traversed in one period for all the sub-jumps is given by:

$$N_J \cdot Y_J + N_{J-1} \cdot Y_{J-1} \quad (15)$$

Expression (15) can be simplified, using expressions (11), (12) and (13) as follows:

$$N_J \cdot Y_J + N_{J-1} \cdot Y_{J-1} = \quad (16)$$
$$(N_J \cdot J + N_{J-1} \cdot (J-1)) \cdot \frac{D_y}{D} = ((E \cdot Ncell - F) \cdot J + F(J-1)) \cdot \frac{D_y}{D} =$$
$$(E \cdot J \cdot Ncell - F) \cdot \frac{D_y}{D} = (E \cdot Nby - F) \frac{D_y}{D} = D_y$$

Expression (16) shows that the total distance traversed by all the sub-jumps is $D_y$; since, as described above, each period begins on the same cell as the previous period, die periodicity is maintained.

Below are numerical examples illustrating the expressions (11)-(16). The following values are assumed:

$D_y$=15.4 mm=15,400 μm;

Nby=48;

Pitch=10 μm;

Ncell=16; and

J=3.

Expressions (12) are satisfied by the values: {d, D, E, F}={0, 1540, 33, 44} and {d, D, E, F}={10, 1539, 33, 45}; these values are respectively referred to below as Example I and Example II.

Expressions (13) generate the following values:

Example I: $N_J$=484, $Y_J$=30 μm;

$N_{J-1}$=44, $Y_{J-1}$=20 μm.

Example II: $N_J$=483, $Y_J$=30.019 μm;

$N_{J-1}$=45, $Y_{J-1}$=20.013 μm.

For both examples, the distance $Y_{stage}$ given by expression (14) is $Y_{stage}$=29.167 μm.

Both examples illustrate that by using two sub-jumps, one having a value greater than $Y_{stage}$, the other having a value less than $Y_{stage}$, die periodicity may be maintained.

In performing a scan of surface 22, the two sub-jumps calculated above may be interspersed in any convenient manner. Typically, the interspersion is performed so that array 27 deviates as little as possible from axis 29 of apparatus 10. Methods for calculating such interspersion are well known in the art; following are two Matlab functions that may be used to calculate a satisfactory interspersion:

```
function [NJ, NJ1, Ystage, YJ, YJ1, overhead] = APBS_algo(Dy, pitch, J, Ncell);
D = fix(Dy / pitch); d = Dy - D*pitch;
NBy = J*Ncell; E = 1 + fix((D-1)/NBy); F = E*NBy - D;
NJ = E*Ncell-F; YJ = J* Dy./D;
NJ1 = F; YJ1 = (J-1)*Dy./D;
N = NJ + NJ1;          % total number of jumps
Ystage = die ./ N;
overhead = (J-1)*d./die + pitch*F./die;
return
function [Jump] = APBS_jump(Dy, pitch, J, Ncell);
% Jump = output vector of optimal jump sequence
%     (example: [J J J-1 J ... ]' )
[NJ, NJ1, Ystage, YJ, YJ1, overhead] = APBS_algo(Dy, pitch, J, Ncell);
N = NJ + NJ1; dY = YJ - Ystage; dY1 = YJ1 - Ystage;
Jump = [J]; Offset = dY;
for i=2:N,
Offset_J = Offset + dY; Offset_J1 = Offset + dY1;
  if abs(Offset_J)< abs(Offset_J1), Jump = [Jump; J]; Offset = Offset_J;
  else Jump = [Jump; J-1]; Offset = Offset_J1;
  end
end
return
```

It will be appreciated that while the description above is generally directed to multiple scanning beam apparatus used for inspection, the scope of the present invention comprises other types of scanning beam apparatus, such as is used for lithography. It will also be appreciated that embodiments of the present invention significantly relax tolerances on beam positions for both optical and particle beams, since there is no relationship between the direction of motion of the scanning stage and the positions of the beams within their array. Furthermore, embodiments of the present invention significantly increase the size of the array that may be used, while enabling the array to be kept within a specific region, such as an aberration-free region. Also, embodiments of the present invention enable die periodicity to be maintained, without compromising on the advantages described above.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. An apparatus for scanning a surface, comprising:
   a beam generator which generates an array of beams;
   beam optics having an optical axis, which are adapted to focus the array of beams so as to irradiate a region of the surface intercepted by the optical axis, wherein each beam irradiates a portion of a respective sub-region within the region;
   a surface translator for moving at least one of the array and the surface so as to cause a surface velocity relative to the optical axis in a first direction; and
   an array scanner, which, during said moving, is adapted to scan each of the beams over the respective sub-region in a second direction, which is different from the first direction, said scanning defining an array of raster patterns, each raster pattern covering a respective sub-region and comprising rows that are perpendicular to said first direction; and said scanning comprising:
      scanning a predetermined number of said rows, and then jumping in a direction substantially opposite to the first direction, so as to repeat said raster pattern over a new region of the surface.

2. The apparatus according to claim 1, wherein the array of raster patterns completely covers the region.

3. The apparatus according to claim 1, wherein the surface comprises dies, and wherein the beam optics have a magnification which is adjusted to maintain a die periodicity.

4. The apparatus according to claim 1, wherein the surface comprises dies, and wherein the jump in the first direction comprises a first and a second jump, and comprising a processor which adjusts a size and a number of the first jump and the size and the number of the second jump so as to maintain a die periodicity.

5. The apparatus according to claim 1, wherein the array of raster patterns partially covers the region.

6. The apparatus according to claim 5, wherein the array scanner is adapted to iteratively repeat the steps of scanning the beams and jumping in the first direction so that the array of raster patterns completely covers the region.

7. The apparatus according to claim 1, wherein the surface translator is adapted to move the surface with a predetermined velocity, and wherein the array scanner is adapted to move the array with an array velocity having a component including the predetermined velocity.

8. The apparatus according to claim 1, wherein the array of beams defines a beam array axis within the region, and wherein said beam array axis and the first direction are independent of each other.

9. The apparatus according to claim 1, wherein the second direction is perpendicular to the first direction.

10. The apparatus according to claim 1, wherein the beam optics define an aberration-corrected region for the beams, and wherein the array scanner and the surface translator are adapted to maintain the region of the surface within the aberration-corrected region.

11. A method for scanning a surface, comprising:
    focusing an array of beams using optics having an optical axis, so as to irradiate a region of the surface intercepted by the optical axis, wherein each beam irradiates a portion of a respective sub-region within the region;
    moving at least one of the array and the surface so as to cause a surface velocity relative to the optical axis in a first direction; and
    during said moving, scanning the array of beams over the region in a second direction, which is different from the first direction, said scanning defining an array of raster patterns, each said raster pattern covering a respective sub-region and comprising rows that are perpendicular to said first direction and said scanning comprising:
       scanning a predetermined number of said rows, and then jumping in a direction substantially opposite to the first direction, so as to repeat said raster pattern over a new region of the surface.

12. The method according to claim 11, wherein the array of raster patterns completely covers the region.

13. The method according to claim 1,1 wherein the surface comprises dies, and said method further comprising adjusting a magnification of the optics to maintain a die periodicity.

14. The method according to claim claim 11 wherein the surface comprises dies, and wherein jumping in the first direction comprises performing a first jump and a second jump, and adjusting a size and a number of the first jump and a size and a number of the second jump so as to maintain a die periodicity.

15. The method according to claim 11 wherein the array of raster patterns partially covers the region.

16. The method according to claim 15, said method further comprising iteratively repeating the steps of scanning the beams and jumping in the first direction so that the array of raster patterns completely covers the region.

17. The method according to claim 11, wherein moving the at least one of the array and the surface comprises moving the surface with a predetermined velocity, and moving the array with an array velocity having a component including the predetermined velocity.

18. The method according to claim 11, wherein the array of beams defines a beam array axis within the region, and wherein said beam array axis and the first direction are independent of each other.

19. The method according to claim 11, wherein the second direction is perpendicular to the first direction.

20. The method according to claim 11, wherein the optics define an aberration-corrected region for the beams, and wherein moving the at least one of the array and the surface comprises maintaining the region of the surface within the aberration-corrected region.

* * * * *